(12) United States Patent
Bainbridge et al.

(10) Patent No.: US 12,728,191 B2
(45) Date of Patent: Sep. 8, 2026

(54) METHODS FOR BLOOD COMPONENT COLLECTION

(71) Applicant: Terumo BCT, Inc., Lakewood, CO (US)

(72) Inventors: Marlene Bainbridge, Lakewood, CO (US); Scott Butzke, Littleton, CO (US)

(73) Assignee: Terumo BCT, Inc., Lakewood, CO (US)

( * ) Notice: Subject to any disclaimer, the term of this patent is extended or adjusted under 35 U.S.C. 154(b) by 420 days.

(21) Appl. No.: 18/216,686

(22) Filed: Jun. 30, 2023

(65) Prior Publication Data

US 2025/0001063 A1 Jan. 2, 2025

(51) Int. Cl.
*A61M 1/38* (2006.01)
*A61M 1/34* (2006.01)

(52) U.S. Cl.
CPC ............ *A61M 1/38* (2013.01); *A61M 1/3496* (2013.01); *A61M 1/385* (2013.01); *A61M 1/387* (2013.01); *A61M 2202/0415* (2013.01); *A61M 2202/0427* (2013.01)

(58) Field of Classification Search
CPC .................... A61M 1/38; A61M 1/385; A61M 2202/0415; A61M 2202/0427; A61M 2205/33; A61M 2230/005
See application file for complete search history.

(56) References Cited

U.S. PATENT DOCUMENTS

2010/0042037 A1 2/2010 Felt et al.
2021/0187182 A1 6/2021 Patel et al.
2023/0285644 A1 * 9/2023 Pittinger ................ G16H 20/40

FOREIGN PATENT DOCUMENTS

CN 115753506 A * 3/2023

OTHER PUBLICATIONS

Written Opinion for corresponding International Patent Application No. PCT/US2024/023374 dated Aug. 7, 2024 (7 Pages).
International Search Report for corresponding International Patent Application No. PCT/US2024/023374 dated Aug. 7, 2024 (2 Pages).

* cited by examiner

*Primary Examiner* — Leslie R Deak
(74) *Attorney, Agent, or Firm* — Harness, Dickey & Pierce, P.L.C.

(57) ABSTRACT

A method for collecting blood components includes separating a first amount of plasma from whole blood; separating a total amount of collectable platelets from the whole blood as available after the separation of the first amount of plasma; if a total collected amount is less than a maximum as adjusted by real-time data regarding collection following the separation of the total amount of platelets, separating a second amount of plasma from the whole blood as available after the separation of the total amount of platelets and then separating a total amount of red blood cells from the whole blood as available after the separation of the second amount of plasma; and if the total collected amount is at the maximum as adjusted by real-time data regarding collection, separating the total amount of red blood cells from the whole blood as available after the separation of the total amount of platelets.

19 Claims, 1 Drawing Sheet

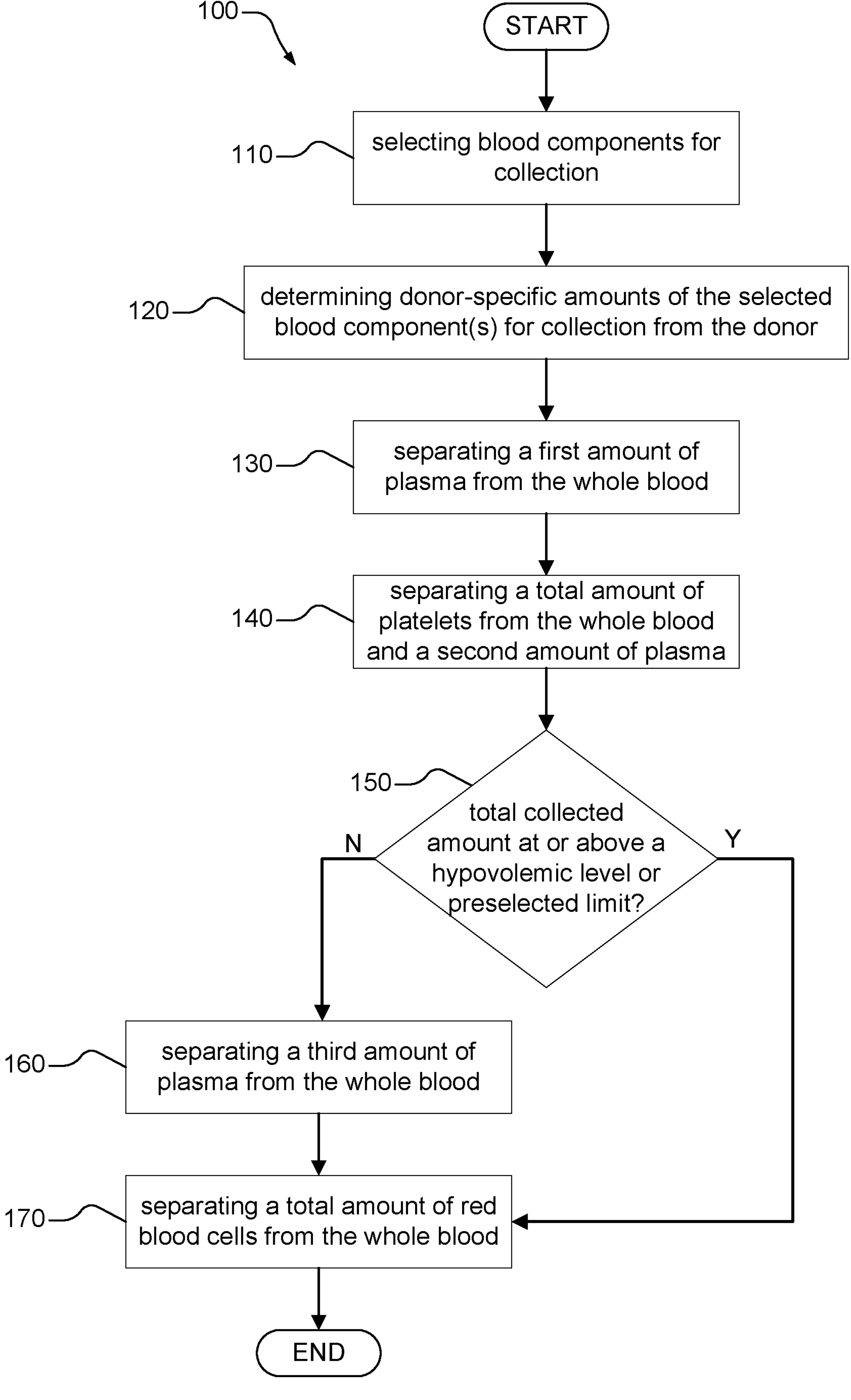
100
START
110
selecting blood components for collection
120
determining donor-specific amounts of the selected blood component(s) for collection from the donor
130
separating a first amount of plasma from the whole blood
140
separating a total amount of platelets from the whole blood and a second amount of plasma
150
total collected amount at or above a hypovolemic level or preselected limit?
N
Y
160
separating a third amount of plasma from the whole blood
170
separating a total amount of red blood cells from the whole blood
END

METHODS FOR BLOOD COMPONENT COLLECTION

FIELD

The present disclosure relates to methods for blood component collection using blood collection systems.

BACKGROUND

This section provides background information related to the present disclosure which is not necessarily prior art.

Blood collection systems for collecting blood from healthy donors for later emergency and/or medical treatment and/or therapeutic uses generally fall into two broad categories: manual blood collection systems and automated blood collection systems. Manual blood collection systems are those commonly seen and used, for example, in community blood drives, where blood from healthy donors is collected by gravity flow into one or more blood collection containers and later separated (using, for example, centrifuge systems) into one or more components, such as red blood cells, plasma, and/or platelets, which are then used for the emergency and/or medical treatment and/or therapeutic uses. Automated blood collection systems, however, use a specialized machine to separate the collected blood into the one or more components as it is collected from the donor. In certain variations, the automated blood collection systems may push back to the donor the unselected components of the one or more components.

Often, automated blood collection systems include prediction function software or programs that use information received and/or collected about the donor to determine appropriate flow rates and volumes that should result in final products that are within the limits of volumes, concentration, and ending cells counts for the individual donor as determined by government and/or blood center regulations and guidelines. Automated blood collection systems are also often configured to continuously monitor and tune and the collection process using the real time data to maintain accepted donation levels (usually referred to as the hypovolemic limit). The calculated volume of red blood cells is often the same as the tuned volume actually collected. However, platelet collection is often limited in real time because plasma collection finishes (i.e., predicted volumes collected) first and triggers hypovolemic limits often causing the automated blood collected systems to end collection and initiate rinseback, which pushes remaining blood components back to the donor. Accordingly, it may be desirable to develop systems and methods of using the same that can prioritize the often more desired platelet collection over plasma collection.

SUMMARY

This section provides a general summary of the disclosure and is not a comprehensive disclosure of its full scope or all of its features.

In at least one example embodiment, the present disclosure provides a method for using an automated blood collection systems to collect blood components from a subject. The method may include separating a first amount of plasma from whole blood received from the subject; following the separation of the first amount of plasma from the whole blood, separating a total amount of collectable platelets from the whole blood as available after the separation of the first amount of plasma; and following the separation of the total amount of platelet, separating a second amount of plasma from the whole blood as available after the separation of the total amount of platelets.

In at least one example embodiment, the first amount of plasma may be a total amount of collectable plasma less than greater than or equal to about 8 millimeters to less than or equal to about 25 milliliters. The total amount of collectable plasma may be determined by a hypovolemic level or a pre-selected maximum for the subject as adjusted by real-time data regarding collection.

In at least one example embodiment, the method may further include at least one of determining the total amount of collectable plasma and determining the first amount of plasma.

In at least one example embodiment, the first amount of plasma may be a total amount of collectable plasma less than about 10 milliliters. The total amount of collectable plasma ay be determined by a hypovolemic level or a pre-selected maximum for the subject as adjusted by real-time data regarding collection.

In at least one example embodiment, the second amount of plasma may be greater than or equal to about 8 millimeters to less than or equal to about 25 milliliters.

In at least one example embodiment, the method may further include, following the separation of the total amount of platelet and before the separating of the second amount of plasma, determining if a total collected amount has reached a hypovolemic level or a pre-selected maximum for the subject as adjusted by real-time data regarding collection.

In at least one example embodiment, the method may further include determining the second amount of plasma to be separated based on the relationship of a total collected amount to a hypovolemic level or a pre-selected maximum for the subject as adjusted by real-time data regarding collection.

In at least one example embodiment, the method may further include, following the separation of the second amount of plasma, separating a total amount of red blood cells from the whole blood as available after the separation of the second amount of plasma.

In at least one example embodiment, the present disclosure provides a method for using an automated blood collection system to collect blood components from a subject. The method may include separating a first amount of plasma from whole blood received from the subject; following the separation of the first amount of plasma from the whole blood, separating a total amount of collectable platelets from the whole blood as available after the separation of the first amount of plasma; if a total collected amount is less than a hypovolemic level or a pre-selected maximum for the subject as adjusted by real-time data regarding collection following the separation of the total amount of platelets, separating a second amount of plasma from the whole blood as available after the separation of the total amount of platelets and then separating a total amount of red blood cells from the whole blood as available after the separation of the second amount of plasma; and if the total collected amount is at the hypovolemic level or the pre-selected maximum for the subject as adjusted by real-time data regarding collection, separating the total amount of red blood cells from the whole blood as available after the separation of the total amount of platelets.

In at least one example embodiment, the method may further include determining if the total collected amount is less than or at the hypovolemic level or the pre-selected maximum for the subject as adjusted by real-time data regarding collection.

In at least one example embodiment, the first amount of plasma may be a total amount of collectable plasma less than greater than or equal to about 8 millimeters to less than or equal to about 25 milliliters. The total amount of collectable plasma may be determined by the hypovolemic level or the pre-selected maximum for the subject as adjusted by real-time data regarding collection.

In at least one example embodiment, the method may further include determining at least one of the total amount of collectable plasma and the first amount of plasma.

In at least one example embodiment, the first amount of plasma may be a total amount of collectable plasma less than about 10 milliliters. The total amount of collectable plasma being determined by the hypovolemic level or the pre-selected maximum for the subject as adjusted by real-time data regarding collection.

In at least one example embodiment, the method may further include determining the second amount of plasma to be separated based on the hypovolemic level or the pre-selected maximum for the subject as adjusted by real-time data regarding collection.

In at least one example embodiment, the present disclosure may provide a protocol for an automated blood collection system configured to collect blood components from a subject. The protocol may include a pre-platelet plasma collection phase, a platelet collection phase that follows the pre-platelet plasma collection phase, and a post-platelet plasma collection phase that follows the platelet collection phase. The pre-platelet plasma collection phase may include separating a first amount of plasma from whole blood received from the subject. The platelet collection phase may include separating a total amount of collectable platelets from the whole blood as available after the separation of the first amount of plasma. The post-platelet plasma collection phase may include separating a second amount of plasma from the whole blood as available after the separation of the total amount of platelets.

In at least one example embodiment, the first amount of plasma may be a total amount of collectable plasma less than greater than or equal to about 8 millimeters to less than or equal to about 25 milliliters. The total amount of collectable plasma may be determined by a hypovolemic level or a pre-selected maximum for the subject as adjusted by real-time data regarding collection.

In at least one example embodiment, the first amount of plasma may be a total amount of collectable plasma less than about 10 milliliters. The total amount of collectable plasma may be determined by the hypovolemic level or the pre-selected maximum for the subject as adjusted by real-time data regarding collection.

In at least one example embodiment, the protocol may further include, following the platelet collection phase and before the post-platelet plasma collection phase, a calculation phase. The calculation phase may include determining if a total collected amount is less than or at a hypovolemic level or a pre-selected maximum for the subject as adjusted by real-time data regarding collection. The total collected amount, which may also be referred to as a total donated amount or a total donation amount, refers to a volume collected up to the noted point in the donation or collection cycle.

In at least one example embodiment, the calculation phase may also include determining the second amount of plasma to be separated based on the hypovolemic level or a pre-selected maximum for the subject as adjusted by real-time data regarding collection.

In at least one example embodiment, the protocol may further include a red blood cell phase. The red blood cell phase may include separating a total amount of red blood cells from the whole blood as available after the separation of the second amount of plasma.

Further areas of applicability will become apparent from the description provided herein. The description and specific examples in this summary are intended for purposes of illustration only and are not intended to limit the scope of the present disclosure.

DRAWING

The drawing described herein are for illustrative purposes only of selected embodiments and not all possible implementations and are not intended to limit the scope of the present disclosure.

FIG. 1 is a flowchart illustrating an example method for using an automated blood collection system in accordance with at least one example embodiment of the present disclosure.

DETAILED DESCRIPTION

Example embodiments will now be described more fully with reference to the accompanying drawing.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having" are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected, or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers, and/or sections, these elements, components, regions, layers, and/or sections should not be limited by these terms. These terms may be only used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the FIGURES. Spatially relative terms may be intended to encompass different orientations of the device in use or operation in addition to the orientation depicted in the figures. For example, if the device in the FIGURES is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Various components are referred to herein as "operably associated." As used herein, "operably associated" refers to components that are linked together in operable fashion and encompasses embodiments in which components are linked directly, as well as embodiments in which additional components are placed between the linked components. "Operably associated" components can be "fluidly associated." "Fluidly associated" refers to components that are linked together such that fluid can be transported between them. "Fluidly associated" encompasses embodiments in which additional components are disposed between the two fluidly associated components, as well as components that are directly connected. Fluidly associated components can include components that do not contact fluid but contact other components to manipulate the system (e.g., a peristaltic pump that pumps fluids through flexible tubing by compressing the exterior of the tube).

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some example embodiments, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

Example embodiments will now be described more fully with reference to the accompanying drawing.

The present disclosure relates to methods of and means for collecting one or more blood components, like platelets, red blood cells, and/or plasma, using an automated blood collection system, like the blood collection systems described in U.S. Pat. No. 10,585,085, titled COLLECTING COMPONENTS OF A FLUID and issued Mar. 10, 2020 and/or U.S. Pat. No. 9,758,764, titled SEPARATING COMPOSITE LIQUIDS and issued Sep. 12, 2017 and/or U.S. Pat. No. 10,618,060, titled CENTRIFUGE SAFETY MECHANISM and issued Apr. 14, 202 and/or U.S. Pat. No. 10,166,322, titled GAIN IN SEPARATION PROCESSES WITH CONTROL LOOP and issued Jan. 1, 2019 and/or U.S. Pat. No. 9,440,011, titled HYBRID BLOOD COMPONENT STORAGE BAG AND METHOD OF MAKING SUCH BAG and issued Sep. 13, 2016 and/or U.S. Pat. No. 8,523,750, titled METHOD AND APPARATUS FOR EXTRACTING PLATELETS WITH REDUCED PLASMA CARRYOVER and issued Sep. 3, 2013 and/or U.S. Pat. No. 8,123,713, titled SYSTEM AND METHODS FOR COLLECTING PLASMA PROTEIN FRACTIONS FROM SEPARATED BLOOD COMPONENTS and issued Feb. 28, 2012 and/or U.S. Pat. No. 7,780,618, titled EXTRACORPOREAL BLOOD PROCESSING APPARATUS AND METHODS WITH PRESSURE SENSING and issued Aug. 24, 2010, the entire disclosures of which are hereby incorporated by references. Methods of using automated blood collection systems often generally include collecting whole blood from a donor or subject, separating the whole blood into one or more selected components (like platelets, red blood cells, and plasma), and pushing back other components not selected (like white blood cells) back to the donor or subject.

FIG. 1 illustrates an example method 100 for using automated blood collection systems. The method 100 may include selecting 110 blood components for collection and determining 120 donor-specific safe amounts or volumes of the selected blood component(s) for collection from the donor. The determining 120 may include performing an initial calculation before collection begins and also ongoing calculations using real time data to ensure that safe and acceptable levels are observed. The donor-specific safe amounts or volumes of the selected blood component(s) for collection from the donor may be determined using user or donor inputs or stored information (such as, sex, height, weight, hematocrit, and/or platelet count) and also measured information from the ongoing collection (such as, inlet volume and/or blood volumes thus far collected). The automated blood collection systems (and more specifically, controls or programs therein) may be configured to alter one or more parameters (such as flow rate) in response to the initial calculation and also the ongoing calculations. When levels reach or are near preselected levels (e.g., a hypovolemic limit) as set, for example, by governmental and/or blood center regulations and guidelines, the automated blood collection systems (and more specifically, controls or programs therein) may be configured to generate an alert for the provider or user or operator and/or to initiate rinseback.

When plasma and platelets are identified for collection, the method 100 may enter a pre-platelet or first plasma collection (PC) phase that includes separating or collecting 130 a pre-platelet or first amount or volume of plasma from the whole blood (using, for example, a centrifugal process) as it is received from the donor. The pre-platelet plasma collection phase occurs before enough platelets have been gathered or built up for collection. The first amount of plasma is less than a total amount or volume of collectable plasma as initially calculated and/or tuned (for example, during the ongoing calculations) for the individual donor in accordance with government and/or blood center regulations and guidelines. For example, in at least one example embodiment, the first amount may be a total amount of collectable plasma less than greater than or equal to about 8 millimeters (mL) to less than or equal to about 25 milliliters. In at least one example embodiment, the first amount may be a total amount of collectable plasma less than about 10 milliliters. It should be appreciated that the total amount of collectable plasma may be continuously adjusted in response to new information collected or received regarding the ongoing collection process, including during the pre-platelet collection phase. The total amount of collectable plasma used to determine the first amount is the total amount of collectable plasma as available and understood at the decision-making point.

Following (or during a later portion of) the pre-platelet plasma collection phase, the method 100 may enter a platelet collection phase that includes separating or collecting 140 a total amount or volume of platelets from the whole blood (using, for example, a centrifugal process) from the whole blood as available after (or during a later part of) the pre-platelet plasma collection phase (e.g., after the removal or extraction or collection or separation of the first amount of plasma). The total amount of collectable platelets may be as initially calculated and/or tuned (for example, during the ongoing calculations) for the individual donor in accordance with government and/or blood center regulations and guidelines. It should be appreciated that the total amount of collectable platelets may be continuously adjusted in response to new information collected or received regarding the ongoing collection process, including during the platelet collection phase. It should also be appreciated that a second amount or volume of plasma may also be collected from the whole blood as available after the removal or extraction or collection or separation of the first amount of plasma during the pre-platelet plasma collection phase.

Following (or during a later portion of) the platelet collection phase, the method 100 may enter an extended or post-platelet or second plasma collection (PC) phase and/or a red blood cell collection phase.

The extended plasma collection phase may include separating or collecting 160 a post-platelet or third amount or volume of plasma from the whole blood (using, for example, a centrifugal process) from the whole blood as available after (or during a later part of) the pre-platelet plasma collection phase (e.g., after the removal or extraction or collection or separation of the total amount of platelet and the removal or extraction or collection or separation of the second amount of plasma).

The red blood cell collection phase may include separating or collecting 170 a total amount of collectable red blood cells from the whole blood (using, for example, a centrifugal process) as available after (or during a later part of) the pre-platelet plasma collection phase (e.g., after the removal or extraction or collection or separation of the total amount of platelet and the removal or extraction or collection or separation of the second amount of plasma) and/or as available after (or during a later part of) the extended plasma collection phase (e.g., after the removal or extraction or collection or separation of the third amount of plasma).

As illustrated, in FIG. 1, the method 100 will proceed to the extended plasma collection phase if it is determined at the decision point 150 that the real-time data indicates that actual collected levels of plasma and platelets until the decision-making point and the expected collected amount of red blood cell are individually and collectively below safe and acceptable limits (i.e., under the hypovolemic limit) and/or under preselected or default limit. Thus, the collection of and the volume of the third amount of the plasma depends upon space remaining within the acceptable limits (i.e., under the hypovolemic limit) and/or under a preselected or default limit. In at least one example embodiment, the third amount of plasma may include greater than or equal to about 8 millimeters to less than or equal to about 25 milliliters, and in certain aspects, optionally about 10 milliliters of plasma.

In contrast, if the real-time data indicates, at the decision point 150, that actual collected levels of plasma and platelets up until the decision-making point and the expected collected amount of red blood cell are at or near the safe and acceptable limit (i.e., under the hypovolemic limit) and/or under the preselected or default limit, the method 100 will bypass the second collection of plasma and proceed to the red blood cell collection phase. This protocol allows maximum amounts of the prefer platelets to be collected while operating under the hypovolemic limit and/or the preselected or default limit.

Although not illustrated, it should be appreciated that in various embodiments, the present disclosure may include one or more other steps or phases as known to the skilled artisan.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for using an automated blood collection system to collect blood components from a source, the method comprising:

receiving whole blood from the source;

separating the whole blood into a first component and a mixed component, the first component being plasma;

after or concurrent with the separating of the whole blood into the first component and the mixed component, removing a first portion of the first component;

after the removing of the first portion of the first component, separating a second portion of the first component and the mixed component into a second component and a third component, the second component including platelets, the first portion of the first component being a total amount of the first component less the second portion of the first component, the total amount of the first component being determined by a hypovolemic level or a pre-selected maximum for the source as adjusted by real-time data regarding the collection of the blood components from the source using the automated blood collection system;

after or concurrent with the separating of the second portion of the first component and the mixed component into the second component and the third component, removing the second component in its entirety; and after the removing of the second component, separating the third component into the second portion of the first component and a fourth component.

2. The method of claim 1, wherein the second portion of the first component is within a range of greater than or equal to about 8 millimeters to less than or equal to about 25 milliliters.

3. The method of claim 1, further comprising:

at least one of determining the total amount of collectable plasma and determining an amount of the first portion of the first component.

4. The method of claim 1, wherein the first portion of the first component is a total amount of collectable plasma less about 10 milliliters.

5. The method of claim 1, further comprising:

following the removing of the second component and before the separating of the third component into the second portion of the first component and the fourth component, determining if a total collected amount has reached the hypovolemic level or the pre-selected maximum for the source as adjusted by the real-time data, the total collected amount being the first portion of the first component plus the second component.

6. The method of claim 1, further comprising:

determining an amount of the second portion of the first component to be separated based on a relationship of a total collected amount to the hypovolemic level or the pre-selected maximum for the source as adjusted by the real-time data, the total collected amount being the first portion of the first component plus the second component.

7. The method of claim 1, further comprising:

separating the fourth component into a fifth component and a residual mix; and removing the fifth component.

8. A method for using an automated blood collection system to collect blood components from a source, the method comprising:

receiving whole blood from the source;

separating the whole blood into a first component and a second component;

after the separating of the whole blood into the first component and the second component, separating the second component and a second portion of the first component into a third component and a fourth component;

after the separating of the second component and the second portion of the first component into the third component and the fourth component, removing the third component in its entirety;

if a total collected amount is less than a hypovolemic level or a pre-selected maximum for the source as adjusted by real-time data regarding the collection of the blood component from the source using the automated blood collection system following the removing of the third component, separating the fourth component into the second portion of the first component and a fifth component, then removing the second portion of the first component, and then separating the fifth component into a sixth component and a residual mix and removing the sixth component; and if the total collected amount is at the hypovolemic level or the pre-selected maximum for the source as adjusted by the real-time data, separating the fourth component into the second portion of the first component, the sixth component, and the residual mix and then removing the sixth component.

9. The method of claim 8, wherein the first component includes plasma, the second component includes platelets, and the sixth component includes red blood cells.

10. The method of claim 8, wherein an amount of the first portion of the first component is a total amount of collectable plasma less the second portion of the first component, the second portion of the first component being greater than or equal to about 8 millimeters to less than or equal to about 25 milliliters, the total amount of collectable plasma being determined by the hypovolemic level or the pre-selected maximum for the source as adjusted by the real-time data.

11. The method of claim 10, further comprising:

determining at least one of the total amount of collectable plasma and the amount of the first portion of the first component.

12. The method of claim 8, wherein the first portion of the first component is about 10 mL less than a total amount of the first component, the total amount of the first component being determined by the hypovolemic level or the pre-selected maximum for the source as adjusted by the real-time data regarding collection.

13. The method of claim 8, further comprising:

determining an amount of the second portion of the first component to be separated based on the hypovolemic level or the pre-selected maximum for the source as adjusted by the real-time data.

14. A protocol for an automated blood collection system configured to collect blood components from a source, the protocol comprising:

a pre-platelet collection phase that includes separating a first amount of a first component from whole blood received from the source;

a platelet collection phase that includes separating a total amount of collectable platelets from the whole blood as available after the pre-platelet collection phase; and a post-platelet collection phase that includes separating a second amount of a first component from the whole blood as available after the platelet collection phase, the first amount being a total amount of collectable first component less the second amount of the first component, the total amount of collectable first component being determined by a hypovolemic level or a pre-selected maximum for the source as adjusted by real-time data regarding the collection of the blood components from the source using the automated blood collection system.

15. The protocol of claim 14, wherein the second amount of the first component being within a range greater than or equal to about 8 millimeters to less than or equal to about 25 milliliters.

16. The protocol of claim 14, wherein the second amount of the first component is about 10 milliliters.

17. The protocol of claim 14, further comprising:

following the platelet collection phase and before the post-platelet collection phase, a calculation phase that includes determining if a total collected amount is less than or at the hypovolemic level or the pre-selected maximum for the source as adjusted by the real-time data.

18. The protocol of claim 17, wherein the calculation phase includes determining the second amount of the first component to be separated based on the hypovolemic level or the pre-selected maximum for the source as adjusted by the real-time data.

19. The protocol of claim 14, wherein the post-platelet collection phase includes separating a second component from the whole blood as available after the separation of the second amount of the first component.

* * * * *